US005866764A

United States Patent [19]
Gabor et al.

[11] Patent Number: 5,866,764
[45] Date of Patent: Feb. 2, 1999

[54] ***LYCOPERSICON PIMPINELLIFOLIUM* AS A SOURCE OF RESISTANCE TO THE PLANT PATHOGEN *PHYTOPHTHORA INFESTANS***

[75] Inventors: Brad Kane Gabor, Woodland; Douglas Heath, Rocklin, both of Calif.; Jon Craig Watterson, Junas, France; Steven Mark Barineau, Fort Myers, Fla.

[73] Assignee: Seminis Vegetable Seeds, Inc., Saticoy, Calif.

[21] Appl. No.: 621,352

[22] Filed: Mar. 25, 1996

[51] Int. Cl.$^{6}$ .............................. A01H 1/04; A01H 5/00; A01H 5/10

[52] U.S. Cl. .......................... 800/200; 800/250; 800/255; 800/DIG. 44; 47/58; 47/DIG. 1

[58] Field of Search .................................... 800/200, 250, 800/255, DIG. 44; 47/58, DIG. 1

[56] References Cited

U.S. PATENT DOCUMENTS

| | | | |
|---|---|---|---|
| 4,634,674 | 1/1987 | Shahin | 435/240 |
| 4,734,369 | 3/1988 | Evans et al. | 435/240.49 |
| 4,818,699 | 4/1989 | Evans et al. | 435/240.49 |
| 4,827,079 | 5/1989 | Evans et al. | 800/1 |
| 4,863,863 | 9/1989 | Cocking et al. | 435/172.1 |
| 4,935,339 | 6/1990 | Evans et al. | 800/1 |
| 4,940,839 | 7/1990 | Bravo et al. | 800/220 |
| 5,053,331 | 10/1991 | Clarke et al. | 435/172.1 |
| 5,126,263 | 6/1992 | Cocking | 435/240.47 |
| 5,225,341 | 7/1993 | Yoder et al. | 435/172.3 |
| 5,254,800 | 10/1993 | Bird et al. | 800/205 |
| 5,254,801 | 10/1993 | Dotson et al. | 800/205 |
| 5,385,835 | 1/1995 | Helentjaris et al. | 435/172.3 |
| 5,387,757 | 2/1995 | Bridges et al. | 800/205 |
| 5,422,108 | 6/1995 | Mirkov et al. | 424/94.61 |
| 5,438,152 | 8/1995 | Morrison et al. | 800/200 |

OTHER PUBLICATIONS

Khrustaleva et al. Resistance to Phytophthora in mutant lines of currant tomato and in their orginal forms. Mutation Breeding Newsletter. No. 30, pp. 7–8, 1987.

Tigchelaar. Tomato Breeding. In: Breeding Vegetable Crops. Ed. Bassett. The Avi Publishing Company,Inc., 1986.

Saccardo, F. et al., "Useful traits transferred in processed tomatoes through interspecific crosses", *Acta Horticulturae,* No. 200, 1987, p. 203.

Alpatev, A. et al., "Evaluating mutant lines of currant tomato, wild species and semicultivated botanical varieties", *Selektsiva Ovoshchnykh Kul'tur,* 1984, Moscow, pp. 49–54.

Korobchuk, V.I., "Possibilities of using mutants of *Lycopersicon pimpinellifolium* to obtain high–yielding first–generation hybrids", *Byulleten Vsesoyuznogo Ordena Lenina I Ordena Druzhby Narodov,* No. 99, 1980, pp. 74–76.

Vozhdova, G. et al., "Genetical analysis of the resistance to tomato fruits to *Phytophtora infestans*", *Acta Universitatis Agriculturae Brno,* vol. 32, No. 4, 1984, pp. 283–288.

Koop, H–U. et al., "Electric Field Induced Fusion and Cell Reconstitution with preselected Single Protoplasts and Subportoplasts of Higher Plants", *Electroporation and Electrofusion in Cell Biology,* 1989, pp. 355–365.

Gallegly, 1960. *ResIstance To The Late Blight Fungus In Tomato, Campbell Plant Sciences Seminar.* pp. 113–135.

*Asian Vegetable Research And Develpment Center,* 1993. *Screening Lycopersicon Accessions For Resistance To Late Blight AVRDC Progress Report* 1993. pp. 201–203.

*Primary Examiner*—Douglas W. Robinson
*Assistant Examiner*—Melissa L. Kimball
*Attorney, Agent, or Firm*—Rockey, Milnamow & Katz

[57] ABSTRACT

The present invention involves tomato plants (*Lycopersicon esculentum*) that are resistant to the tomato strain of *P. infestans* races 0 and 1. *Lycopersicon pimpinellifolium* plants which are resistant to the tomato strain of *P. infestans* races 0 and 1 are used to construct the tomato plants of the present invention. The preferred *Lycopersicon pimpinellifolium* used in the present invention is designated as LA 2533.

13 Claims, No Drawings

LYCOPERSICON PIMPINELLIFOLIUM AS A SOURCE OF RESISTANCE TO THE PLANT PATHOGEN *PHYTOPHTHORA INFESTANS*

BACKGROUND OF THE INVENTION

For more than a century, late blight on tomato and potato plants has been a cause of concern to plant breeders. Late blight is common in areas that have cool wet weather and it can be devastating during the rainy season when the humidity is high. Although late blight is a worldwide problem, it is particularly prevalent in the eastern United States, Mexico and the Far East.

Late blight is caused by a fungus called *Phytophthora infestans* ("*P. infestans*"). *Phytophthora infestans* can survive on plant debris, potato tubers, and also on Solanaceous weeds. Spores of this fungus are typically disseminated during windy, rainy periods; however, the fungus can be disseminated on infected plant debris and fruit. Upon landing on the leaves, stems and fruit of tomato plants, spores can rapidly infect the plant tissues causing tissue collapse and eventual death of the plant.

Presently, there have been two physiologic races described for *P. infestans* in tomato. The first is *P. infestans* race 0 which is pathogenic on commercial varieties that contain no resistance genes. The second is *P. infestans* race 1 which is pathogenic on commercial varieties that contain the $Ph_1$, resistance gene.

In 1952, resistance to *P. infestans* was reported in a wild tomato relative, *Lycopersicon pimpinellifolium*. This resistance was found to be conferred by a single dominant gene ($Ph_1$; formerly known as $TR_1$) that gave resistance to the tomato strain of *P. infestans* race 0. However, the tomato strain of *P. infestans* race 1 overcomes the resistance conferred by $Ph_1$. See Gallegly, M. E,. "Resistance to the Late Blight Fungus in Tomato," (1960) Campbell Plant Science Seminar p. 116. In addition, multigenic resistance was identified in the tomato line West Virginia 700 (PI204996). This resistance was not complete and conferred only a tolerance to *P. infestans* race 0 and 1. When the environmental conditions were favorable for *P. infestans* race 1 development, these tolerant plants sustained significant disease.

The cultivated tomato, *Lycopersicon esculentum*, is one of the most important vegetable crops in the United States and worldwide, with several million tons being produced each year in the United States alone. The commercial importance of the crop has necessitated a constant effort to improve cultivated varieties. Therefore, there is a need for cultivated tomato varieties that exhibit disease resistance to *P. infestans* race 1.

It is an object of the present invention to disclose a novel *Lycopersicon pimpinellifolium* cultivar that can be used as a source of resistance to the tomato strain of *P. infestans* race 1. It is a further object of this invention to provide *Lycopersicon esculentum* plants which are resistant to the tomato strain of *P. infestans*, races 0 and 1 and remain resistant to *P. infestans* race 1 in the field when the disease pressure is high.

SUMMARY OF THE INVENTION

The present invention involves a method for producing tomato plants (*Lycopersicon esculentum*) which are resistant to the tomato strain of *P. infestans* races 0 and 1. These plants are produced by crossing a *Lycopersicon pimpinellifolium* plant which was discovered to contain a new allele(s) which confers resistance to *P. infestans* races 0 and 1 with a *Lycopersicon esculentum*. After the cross is made, the seed is collected and regenerated into plants. The resulting plants are evaluated for resistance to the tomato strain of *P. infestans* races 0 and 1. Plants that demonstrate resistance are identified and selected. These selected resistant plants are backcrossed with other *Lycopersicon esculentum* lines displaying desirable phenotypes to obtain commercially acceptable varieties which are resistant to the tomato strain of *P. infestans* races 0 and 1. This method can also be used to produce seeds that result in tomato plants (*Lycopersicon esculentum*) that are resistant to the tomato strain of *P. infestans* races 0 and 1.

The *Lycopersicon pimpinellifolium* selection which was discovered to have novel resistance to *P. infestans* races 0 and 1 and subsequently used in crosses with *L. esculentum* is designated as LA 2533, which has also been referred to by the inventors as Hope 84.

The plants of the present invention can also be produced by protoplast fusion. To produce plants by protoplast fusion, a protoplast from a *Lycopersicon pimpinellifolium* plant which is resistant to the tomato strain of *P. infestans* races 0 and 1 is obtained along with a protoplast from a *Lycopersicon esculentum*. The protoplasts are then fused using standard protoplast fusion procedures which are well known in the art. The resulting allogenic cells are obtained and regenerated into plants which are evaluated for resistance to the tomato strain of *P. infestans* races 0 and 1. Resistant plants are identified and selected.

The *Lycopersicon esculentum* plants produced according to the method of this invention are resistant to the tomato strain of *P. infestans*, races 0 and 1 and remain resistant to *P. infestans* race 1 in the field when the disease pressure is high.

The present invention also involves tomato plants which contain an allele(s) which confers resistance to the tomato strain of *P. infestans* races 0 and 1 and seed produced by said tomato plants.

DETAILED DESCRIPTION OF THE INVENTION

The present invention involves the creation of tomato plants (*Lycopersicon esculentum*) which are resistant to the tomato strains of *P. infestans*. Plants are said to be disease resistant if, when exposed to the tomato strains of *P. infestans*, the plants either fail to exhibit disease symptoms or exhibit substantially reduced symptoms compared to susceptible plants. The plants of the present invention are new and novel because they are resistant to the tomato strain of *P. infestans*, races 0 and 1.

The inventors of the present invention have discovered *Lycopersicon pimpinellifolium* plants which contain an allele(s) that confers resistance to the tomato strain of *P. infestans* races 0 and 1. These *Lycopersicon pimpinellifolium* plants can be used to create tomato plants (*Lycopersicon esculentum*) that are resistant to the tomato strain of *P. infestans* races 0 and 1. For example, *Lycopersicon pimpinellifolium* plants designated as LA 2533 were used to create the plants of the present invention. *Lycopersicon pimpinellifolium* plants designated as LA 2533 have also been referred to as Hope 84 by the inventors. Seeds of LA 2533 (Hope 84) were deposited with the American Type Culture Collection, 12301 Parklawn Drive, Md. 20852, under the provisions of the Budapest Treaty. The seeds were deposited on Dec. 14, 1995 and received ATCC Accession Number 97382. In addition, LA 2533 (Hope 84) is also available from the Rick Center at the University of California-Davis, Davis, Calif. upon request.

The inventors have discovered that LA 2533 plants exhibit resistance to the tomato strain of *P. infestans*, races 0 and 1. Prior to this discovery, resistance to *P. infestans* races 0 and 1 in plants designated as LA 2533 had been unknown. *Lycopersicon pimpinellifolium* plants designated as LA 2533 contain the allele(s) which confers resistance to the tomato strain of *P. infestans* races 0 and 1. However, one skilled in the art would recognize that any *Lycopersicon pimpinellifolium* which contains the allele(s) and is resistant to the tomato strain of *P. infestans* races 0 and 1 can be used in this invention.

The plants of the present invention can be prepared by traditional breeding techniques. For example, seed from *Lycopersicon pimpinellifolium* plants designated as LA 2533 can be used. Seeds of LA 2533 are planted in a greenhouse or in a field. The resulting plants are exposed to the tomato strains of *P. infestans*, races 0 and 1. After sufficient disease pressure, those plants exhibiting the best resistance are selected. Resistance to *P. infestans* races 0 and 1 may be determined in two ways. The first way to determine resistance to *P. infestans* involves using what is called a "greenhouse screen". In a greenhouse screen, tomato seedlings are grown until the fifth true leaf starts to emerge. At this point, the plants are sprayed with a suspension of *P. infestans* race 1 sporangia, at a concentration of 10,000 sporangia per milliliter of solution. After inoculation, the plants are placed in a chamber with 100% humidity for 24 hours. Next, they are removed from the humidity chamber to a greenhouse bench in order to allow the disease to develop. Resistant plants are identified and selected in approximately 7 days. The plants can then be sprayed a second time with a suspension of *P. infestans* race 0 in the same manner. However, many times it is not necessary to test a plant for resistance to *P. infestans* race 0 because it is generally well known by those of ordinary skill in this art that a tomato plant resistant to *P. infestans* race 1 is more likely than not to be resistant to race 0 as well.

The second way of determining resistance to *P. infestans* races 0 and 1 involves a field screen. A field screen involves transplanting seedlings into a field trial where the weather conditions favor natural infection and disease development. Resistant plants are identified and selected after the disease has developed, approximately when the plants start to set fruit.

The inventors of the present invention devised a disease rating scale for evaluating whether the plants produced by the method of this invention are resistant or susceptible to *P. infestans*, races 0 and 1. The disease rating scale is based on a numerical designation from 1 to 5 that is more specifically described as follows: 1 corresponds to no or small lesions on the foliage only; 2 corresponds to no or small lesions on the foliage, expanding foliage lesions and small lesions (2 mm diameter) on the petiole; 3 corresponds to no or small lesions on the foliage, expanding foliage lesions and small lesions (2 mm diameter) on the petiole, plus expanding lesions on the petiole; 4 corresponds to no or small lesions on the foliage, expanding foliage lesions and small lesions (2 mm diameter) on the petiole, expanding lesions on the petiole, plus small lesions (2 mm diameter) on the stem; and 5 corresponds to no or small lesions on the foliage, expanding foliage lesions and small lesions (2 mm diameter) on the petiole, expanding lesions on the petiole, small lesions (2 mm diameter) on the stem, plus expanding lesions on the stem or a dead plant. Plants with a disease rating of less than three are considered resistant, while plants with a disease rating of three or greater are considered susceptible.

Traditionally, most plant breeders do not evaluate, identify and select for tomatoes that exhibit resistance to *P. infestans*. Most breeders do not work with *P. infestans* out of concern that the presence of this fungus might wipe out their entire crop. Instead, most breeders spray fungicides to control *P. infestans* in an effort to keep the fungus from affecting their crops.

The plants that exhibit the best resistance are then crossed with commercial tomato plants (*L. esculentum*) by placing the pollen from one plant on the stigma of the other. After the tomato fruit develops, seed is collected. The seeds are grown into plants and evaluated for disease resistance. Resistant plants are selected and may be backcrossed with commercial tomato plants possessing desirable phenotypic traits such as plant type (determinate vs. indeterminate), fruit size, shape, flavor, color and long shelf life. The backcrossing may be continued until a variety is obtained that possesses desirable phenotypic traits and is resistant to the tomato strains of *P. infestans* races 0 and 1. The resulting plants are stable to *P. infestans* race 1 in the field under high disease pressure.

It is interesting to note that *Lycopersicon esculentum* is cleistogamous. Therefore, it is very unlikely in the wild that cross pollination between *Lycopersicon pimpinellifolium* and *Lycopersicon esculentum* would occur without human technical intervention. It is also unlikely that the identification, selection and backcrossing for the alleles(s) that confer resistance to *P. infestans* races 0 and 1 would occur naturally.

Protoplast fusion can also be used to create the plants of the present invention. For example, a first protoplast is obtained from a *Lycopersicon pimpinellifolium* designated LA 2533 and a second protoplast is obtained from a *Lycopersicon esculentum*. The protoplasts are then fused using traditional protoplast fusion procedures which are well known in the art.

For example, the protoplast fusion may be accomplished by employing polyethylene glycol (PEG) causing agglutination, in the presence of a fusion buffer, i.e., a high pH solution to let the membranes fuse. Such somatic hybridization may be effected under the conditions disclosed by Sundberg et al. (*Plant Science*, 43, (1986) 155), hereby incorporated by reference, for the production of interspecific hybrids or modifications thereof. However, one skilled in the art would recognize that the protoplast fusion can be accomplished in other ways other than using polyethylene glycol (PEG). For example, the protoplasts can be fused by using electric field-induced fusion techniques as described by Koop et al. (1989) "Electric Field-Induced Fusion and Cell Reconstruction-with Preselected Single Protoplasts and Subprotoplasts of Higher Plants" in *Electroporation and Electrofusion in Cell Biology*, Neuman et al. editors, pgs. 355–365, herewith incorporated by reference. Additionally, protoplast fusion can be accomplished with dextran and polyvinyl alcohol as described by Hauptmann et al., "Carrot x Tobacco Somatic Cell Hybrids Selected by Amino Acid Analog Resistance Complementation", 6th International Protoplast Symposium, Basel, Aug. 12–16, 1983, herewith incorporated by reference.

By way of example and not limitation, examples of the present invention will now be given.

EXAMPLE 1

Several different plants were evaluated for possible *P. infestans* resistance. The following seeds were obtained: *L. pimpinellifolium* designated LA 373, *L. esculentum* var.

*cerasiforme* designated as LA 1338, *L. pimpinellifolium* designated LA 1375, *L. hirsutum* designated as LA 2650, and *L. pimpinellifolium* designated as LA 2533 (Hope 84). All of these seeds were obtained from the Rick Center at the University of California-Davis in Davis, Calif. Hope 33 is a tomato line that has tolerance to *P. infestans* race 0 and race 1. Celebrity and Fandango are commercial varieties which do not exhibit any resistance to *P. infestans*.

The seeds were planted in a greenhouse. Tomato seeds were planted into soil (50% peatmoss: 50% sand) and placed on a bench in the greenhouse (75° F. day and 70° F. night temperature) and watered as needed. When the tomato seedlings had reached the fifth true leaf stage they were inoculated with *P. infestans* race 1. The seedlings were sprayed with the suspension of *P. infestans* sporangia at a concentration of 10,000 sporangia per milliliter of solution until run off. After inoculation, the plants were placed in a chamber with 100% humidity for 24 hours. Next, the plants were uncovered and the disease allowed to develop. Resistant plants were identified and selected approximately 7 days after inoculation using the following disease ratings. These same lines mentioned above were also evaluated in the same manner with *P. infestans* race 0.

Disease Rating:

1=No or small lesions on the foliage only.

2=Above, plus expanding foliage lesions and small lesions (2 mm diameter) on the petiole.

3=Above, plus expanding lesions on the petiole.

4=Above, plus small lesions (2 mm diameter) on the stem.

5=Above, plus expanding lesions on the stem or dead plant.

The results of the disease rating are provided in Table 1.

TABLE 1

| HOST | DISEASE RATING | | |
|---|---|---|---|
| | RACE 1 | RACE 0 | # OF PLANTS |
| Hope 33 | 3.0 | 1.0 | 9 |
| Celebrity | 5.0 | 2.3 | 9 |
| Fandango | 5.0 | 2.3 | 9 |
| LA 373 *L. pimpinellifolium* | 5.0 | 3.0 | 6 |
| LA 1338 *L. esculentum* var. *cerasiforme* | 5.0 | 1.3 | 6 |
| LA 1375 *L. pimpinellifolium* | 4.3 | 1.0 | 6 |
| LA 2650 *L. hirsutum f. typicum* | 4.3 | 1.2 | 6 |
| LA 2533 *L. pimpinellifolium* | 1.3 | 1.0 | 6 |

The above Table demonstrates that *L. pimpinellifolium* plants designated as LA 2533 had a high level of resistance to *P. infestans* races 0 and 1 whereas other *L. pimpinellifolium* lines desinated as LA 373 and 1375 did not demonstrate a high level at resistance.

EXAMPLE 2

A *L. pimpinellifolium* plant designated LA 2533 and also referred to as Hope 84, was crossed with a tomato (*L. esculentum*) plant designated Fla 7065. Plant Fla 7065 is determinate, large fruited, uniform green, fresh market, firm inbred breeding line that has been released from Dr. Jay Scott's breeding program at the University of Florida, in Florida. Seeds resulting from this cross (F1) were planted into soil and grown in a greenhouse, and inoculated with *P. infestans* race 1 as previously described in Example 1. All the seedlings from this screen were rated as a 1 or 2 using the same disease rating described in Example 1, indicating that they were resistant to *P. infestans*, races 0 and 1. This suggests that the gene(s) responsible for resistance are inherited in a dominant fashion.

EXAMPLE 3

The F1 plants described in Example 2 were self-pollinated. Seedlings resulting from this (F2) were planted into soil and grown in a greenhouse. After several weeks, the seedlings were transplanted into a field, watered by drip irrigation and allowed to grow to maturity. Prior to flowering, cuttings were taken, transplanted into soil and grown in a greenhouse. Two weeks after the cuttings were taken, they were inoculated with sporangia of *P. infestans*, race 1 (concentration: 10,000 sporangia/milliliter) and placed in a chamber at 100% humidity for 24 hours. After twenty-four hours, the plants were removed and the disease allowed to develop. The cuttings were rated on a disease rating scale of 1–5 after 14 days. The disease ratings used were as follows:

Disease rating:

1=No or small lesions on the foliage only.

2=Above, plus expanding foliage lesions and small lesions (2 mm diameter) on the petiole.

3=Above, plus expanding lesions on the petiole.

4=Above, plus small lesions (2 mm diameter) on the stem.

5=Above, plus expanding lesions on the stem or dead plant.

The rating for the F2 plants are provided in Table 2.

TABLE 2

| Line | # | Mean | Line | # | Mean | Line | # | Mean | Line | # | Mean |
|---|---|---|---|---|---|---|---|---|---|---|---|
| 94FH | 120 | 1.0 | 94FH | 97 | 1.3 | 94FH | 123 | 2.0 | 94FH | 146 | 3.0 |
| 94FH | 126 | 1.0 | 94FH | 109 | 1.4 | 94FH | 189 | 2.0 | 94FH | 180 | 3.2 |
| 94FH | 99 | 1.0 | 94FH | 169 | 1.4 | 94FH | 107 | 2.1 | 94FH | 93 | 3.5 |
| 94FH | 148 | 1.0 | 94FH | 158 | 1.5 | 94FH | 157 | 2.2 | 94FH | 141 | 3.5 |
| 94FH | 151 | 1.0 | 94FH | 156 | 1.5 | 94FH | 94 | 2.2 | 94FH | 125 | 3.7 |
| 94FH | 186 | 1.0 | 94FH | 187 | 1.5 | 94FH | 140 | 2.2 | 94FH | 113 | 3.7 |
| 94FH | 114 | 1.0 | 94FH | 115 | 1.5 | 94FH | 101 | 2.2 | 94FH | 90 | 3.8 |
| 94FH | 98 | 1.0 | 94FH | 104 | 1.5 | 94FH | 165 | 2.3 | 94FH | 116 | 4.0 |
| 94FH | 171 | 1.0 | 94FH | 182 | 1.5 | 94FH | 159 | 2.3 | 94FH | 188 | 4.0 |
| 94FH | 162 | 1.0 | 94FH | 177 | 1.6 | 94FH | 150 | 2.5 | 94FH | 102 | 4.3 |
| 94FH | 172 | 1.0 | 94FH | 183 | 1.6 | 94FH | 92 | 2.5 | 94FH | 155 | 4.3 |
| 94FH | 170 | 1.0 | 94FH | 166 | 1.7 | 94FH | 135 | 2.5 | 94FH | 128 | 4.5 |
| 94FH | 121 | 1.0 | 94FH | 167 | 1.7 | 94FH | 149 | 2.5 | 94FH | 178 | 4.7 |
| 94FH | 127 | 1.0 | 94FH | 124 | 1.7 | 94FH | 142 | 2.5 | 94FH | 96 | 5.0 |
| 94FH | 184 | 1.0 | 94FH | 103 | 1.7 | 94FH | 174 | 2.5 | 94FH | 129 | 5.0 |
| 94FH | 100 | 1.2 | 94FH | 176 | 1.7 | 94FH | 137 | 2.7 | 94FH | 95 | 5.0 |

TABLE 2-continued

| Line | # | Mean | Line | # | Mean | Line | # | Mean | Line | # | Mean |
|---|---|---|---|---|---|---|---|---|---|---|---|
| 94FH | 119 | 1.2 | 94FH | 118 | 1.7 | 94FH | 153 | 2.7 | 94FH | 110 | 5.0 |
| 94FH | 154 | 1.2 | 94FH | 106 | 1.8 | 94FH | 108 | 2.7 | Celebrity | | 5.0 |
| 94FH | 160 | 1.2 | 94FH | 179 | 1.8 | 94FH | 143 | 2.8 | Hope 33 | | 3.2 |
| 94FH | 181 | 1.2 | 94FH | 168 | 1.8 | 94FH | 152 | 3.0 | Hope 84 | | 1.4 |
| 94FH | 185 | 1.2 | 94FH | 164 | 1.8 | 94FH | 117 | 3.0 | | | |
| 94FH | 139 | 1.3 | 94FH | 173 | 1.8 | 94FH | 144 | 3.0 | | | |
| 94FH | 161 | 1.3 | 94FH | 138 | 2.0 | 94FH | 91 | 3.0 | | | |
| 94FH | 111 | 1.3 | 94FH | 175 | 2.0 | 94FH | 105 | 3.0 | | | |
| 94FH | 147 | 1.3 | 94FH | 145 | 2.0 | 94FH | 122 | 3.0 | | | |
| 94FH | 163 | 1.3 | 94FH | 112 | 2.0 | 94FH | 136 | 3.0 | | | |

Those lines with a disease rating of 2.9 or less were considered resistant, while those lines with a disease rating of 3.0 or greater were considered susceptible (71 lines resistant: 24 lines susceptible). The data in table 2 supports the 3:1 resistant to susceptible ratio, which would be expected if the resistance loci was dominantly inherited. However, a number of lines had a disease rating between 2.0–2.8. The inventors believe that it is possible that these lines are heterozygotes. If this is true, then this would suggest that resistance is partially dominant where the homozygous plants have a higher level of resistance than heterozygous plants.

EXAMPLE 4

The F2 plants of Example 3 were self-pollinated. Seedlings resulting from this (F3) were planted into soil and grown in a greenhouse. After several weeks, the seedlings were transplanted into a field where the weather conditions favored natural infection and disease development of $P.\ infestans$ race 1. Severe disease pressure became apparent as the susceptible control plants were dead (Celebrity). Plants were rated on a scale of 1–5 when the plants started to set fruit. The disease ratings used were as follows:

1=No or small lesions on the foliage only.

2=Above, plus expanding foliage lesions and small lesions (2 mm diameter) on the petiole.

3=Above, plus expanding lesions on the petiole.

4=Above, plus small lesions (2 mm diameter) on the stem.

5=Above, plus expanding lesions on the stem or dead plant.

The results are listed below in Table 3.

TABLE 3

| Line # | | | | | | | | | | | | | | | | | | Mean |
|---|---|---|---|---|---|---|---|---|---|---|---|---|---|---|---|---|---|---|
| 94AGH | 103 | 1 | 1 | 1 | 1 | 1 | 1 | 1 | 1 | 1 | 1 | 1 | 1 | 1 | 1 | | | 1.0 |
| 94AGH | 148 | 1 | 1 | 1 | 1 | 1 | 1 | 1 | 1 | 1 | 1 | 1 | 1 | 1 | | | | 1.0 |
| 94AGH | 162 | 1 | 1 | 1 | 1 | 1 | 1 | 1 | 1 | 1 | 1 | 1 | 1 | 1 | 1 | | | 1.0 |
| 94AGH | 187 | 1 | 1 | 1 | 1 | 1 | 1 | 1 | 1 | 1 | 1 | 1 | 1 | | | | | 1.0 |
| 94AGH | 158 | 1 | 1 | 1 | 1 | 1 | 1 | 1 | 1 | 1 | 1 | 1 | 1 | 2 | | | | 1.1 |
| 94AGH | 99 | 1 | 1 | 1 | 1 | 1 | 1 | 1 | 1 | 1 | 2 | | | | | | | 1.1 |
| 94AGH | 184 | 1 | 1 | 1 | 1 | 1 | 1 | 1 | 1 | 1 | 1 | 1 | 1 | 1 | 2 | 2 | | 1.1 |
| 94AGH | 172 | 1 | 1 | 1 | 1 | 1 | 1 | 1 | 1 | 1 | 1 | 1 | 2 | 2 | | | | 1.1 |
| 94AGH | 98 | 1 | 1 | 1 | 1 | 1 | 1 | 1 | 1 | 1 | 1 | 2 | 2 | | | | | 1.1 |
| 94AGH | 157 | 1 | 1 | 1 | 1 | 1 | 1 | 1 | 1 | 1 | 1 | 2 | 2 | | | | | 1.2 |
| 94AGH | 100 | 1 | 1 | 1 | 1 | 1 | 1 | 1 | 1 | 1 | 1 | 1 | 1 | 1 | 2 | 2 | 2 | 1.2 |
| 94AGH | 168 | 1 | 1 | 1 | 1 | 1 | 1 | 1 | 2 | 2 | | | | | | | | 1.2 |
| 94AGH | 114 | 1 | 1 | 1 | 1 | 1 | 1 | 1 | 1 | 1 | 1 | 1 | 2 | 3 | | | | 1.2 |
| 94AGH | 183 | 1 | 1 | 1 | 1 | 1 | 1 | 1 | 1 | 1 | 1 | 2 | 2 | 2 | | | | 1.2 |
| 94AGH | 115 | 1 | 1 | 1 | 1 | 1 | 1 | 1 | 1 | 1 | 2 | 2 | 2 | | | | | 1.2 |
| 94AGH | 186 | 1 | 1 | 1 | 1 | 1 | 1 | 1 | 1 | 1 | 1 | 1 | 3 | 3 | | | | 1.3 |
| 94AGH | 156 | 1 | 1 | 1 | 1 | 1 | 1 | 1 | 1 | 2 | 2 | 3 | | | | | | 1.3 |
| 94AGH | 112 | 1 | 1 | 1 | 1 | 1 | 1 | 1 | 2 | 2 | 3 | | | | | | | 1.3 |
| 94AGH | 119 | 1 | 1 | 1 | 1 | 1 | 1 | 1 | 1 | 2 | 2 | 2 | 3 | | | | | 1.4 |
| 94AGH | 160 | 1 | 1 | 1 | 1 | 1 | 1 | 1 | 1 | 1 | 1 | 2 | 2 | 3 | 3 | | | 1.4 |
| 94AGH | 133 | 1 | 1 | 1 | 1 | 2 | 2 | 2 | 2 | 1 | 1 | 1 | 1 | | | | | 1.4 |
| 94AGH | 167 | 1 | 1 | 1 | 1 | 1 | 1 | 2 | 2 | 3 | | | | | | | | 1.4 |
| 94AGH | 120 | 1 | 1 | 1 | 1 | 1 | 1 | 1 | 1 | 2 | 2 | 2 | 3 | 3 | | | | 1.5 |
| 94AGH | 159 | 1 | 1 | 1 | 1 | 1 | 1 | 2 | 2 | 2 | 3 | 3 | | | | | | 1.6 |
| 94AGH | 170 | 1 | 1 | 1 | 1 | 1 | 1 | 1 | 2 | 3 | 3 | 3 | | | | | | 1.6 |
| 94AGH | 121 | 1 | 1 | 1 | 1 | 1 | 1 | 2 | 2 | 2 | 2 | 3 | 3 | | | | | 1.6 |
| 94AGH | 181 | 1 | 1 | 1 | 1 | 1 | 1 | 1 | 3 | 3 | 3 | 3 | 3 | | | | | 1.8 |
| 94AGH | 109 | 1 | 1 | 1 | 1 | 1 | 2 | 2 | 2 | 2 | 2 | 3 | 3 | 3 | | | | 1.9 |
| 94AGH | 144 | 1 | 1 | 1 | 1 | 1 | 1 | 2 | 3 | 3 | 3 | 3 | 4 | | | | | 1.9 |
| 94AGH | 138 | 1 | 1 | 1 | 1 | 1 | 1 | 2 | 3 | 3 | 3 | 3 | 3 | | | | | 1.9 |
| 94AGH | 97 | 1 | 1 | 2 | 3 | 3 | | | | | | | | | | | | 2 |
| 94AGH | 125 | 1 | 1 | 1 | 1 | 1 | 1 | 2 | 3 | 3 | 3 | 3 | 5 | | | | | 2 |
| 94AGH | 166 | 1 | 1 | 1 | 1 | 2 | 2 | 2 | 3 | 3 | 3 | 3 | | | | | | 2 |
| 94AGH | 174 | 1 | 1 | 1 | 1 | 1 | 1 | 3 | 3 | 3 | 4 | 4 | | | | | | 2 |
| 94AGH | 108 | 1 | 1 | 1 | 1 | 1 | 2 | 2 | 2 | 3 | 3 | 3 | 3 | 4 | | | | 2.1 |
| 94AGH | 137 | 1 | 1 | 1 | 1 | 1 | 2 | 3 | 3 | 3 | 3 | 4 | | | | | | 2.1 |
| 94AGH | 132 | 1 | 1 | 1 | 1 | 1 | 1 | 1 | 2 | 3 | 3 | 3 | 3 | 3 | 3 | 3 | 4 | 2.1 |

TABLE 3-continued

| Line # | | | | | | | | | | | | | | | | | | | | Mean |
|---|---|---|---|---|---|---|---|---|---|---|---|---|---|---|---|---|---|---|---|---|
| 94AGH | 161 | 1 | 1 | 1 | 1 | 1 | 2 | 2 | 2 | 2 | 2 | 3 | 3 | 3 | 3 | 3 | 4 | | | 2.1 |
| 94AGH | 179 | 1 | 1 | 1 | 1 | 1 | 2 | 2 | 3 | 3 | 3 | 3 | 5 | | | | | | | 2.2 |
| 94AGH | 136 | 1 | 1 | 1 | 1 | 1 | 2 | 2 | 2 | 2 | 3 | 3 | 3 | 3 | 3 | 3 | 4 | | | 2.2 |
| 94AGH | 171 | 1 | 1 | 1 | 1 | 1 | 1 | 2 | 2 | 3 | 3 | 3 | 3 | 3 | 3 | 3 | 4 | | | 2.2 |
| 94AGH | 111 | 1 | 1 | 1 | 1 | 1 | 1 | 2 | 2 | 2 | 3 | 3 | 3 | 3 | 5 | 5 | | | | 2.3 |
| 94AGH | 135 | 1 | 1 | 1 | 1 | 2 | 3 | 3 | 3 | 3 | 3 | 3 | 3 | 3 | | | | | | 2.3 |
| 94AGH | 104 | 1 | 1 | 1 | 1 | 1 | 1 | 1 | 2 | 2 | 3 | 3 | 3 | 3 | 3 | 4 | 4 | 5 | | 2.3 |
| 94AGH | 126 | 1 | 1 | 1 | 1 | 2 | 2 | 3 | 3 | 3 | 3 | 3 | 3 | 3 | 3 | | | | | 2.3 |
| 94AGH | 151 | 2 | 2 | 2 | 2 | 2 | 2 | 2 | 2 | 3 | 3 | 3 | 3 | | | | | | | 2.3 |
| 94AGH | 154 | 1 | 1 | 2 | 2 | 2 | 2 | 2 | 2 | 3 | 3 | 3 | 3 | 3 | 3 | | | | | 2.3 |
| 94AGH | 189 | 1 | 1 | 1 | 1 | 2 | 2 | 3 | 3 | 3 | 3 | 3 | 3 | 3 | 3 | | | | | 2.3 |
| 94AGH | 143 | 1 | 1 | 1 | 2 | 2 | 2 | 2 | 2 | 3 | 3 | 3 | 3 | 5 | | | | | | 2.4 |
| 94AGH | 127 | 1 | 1 | 1 | 1 | 1 | 1 | 2 | 3 | 3 | 3 | 3 | 3 | 4 | 4 | 4 | | | | 2.4 |
| 94AGH | 185 | 1 | 1 | 1 | 1 | 1 | 2 | 2 | 2 | 3 | 3 | 3 | 3 | 3 | 4 | 4 | 4 | | | 2.4 |
| 94AGH | 164 | 1 | 2 | 2 | 2 | 2 | 2 | 3 | 3 | 3 | 3 | 4 | | | | | | | | 2.5 |
| 94AGH | 169 | 1 | 1 | 1 | 1 | 2 | 3 | 3 | 3 | 3 | 4 | 4 | 4 | | | | | | | 2.5 |
| 94AGH | 106 | 1 | 1 | 1 | 1 | 1 | 2 | 2 | 2 | 2 | 2 | 3 | 3 | 3 | 4 | 5 | 5 | 5 | | 2.6 |
| 94AGH | 124 | 1 | 1 | 1 | 1 | 1 | 3 | 3 | 3 | 3 | 3 | 3 | 3 | 4 | 4 | 4 | | | | 2.6 |
| 94AGH | 173 | 1 | 1 | 1 | 3 | 3 | 3 | 3 | 3 | 3 | 3 | 3 | 3 | 3 | | | | | | 2.6 |
| 94AGH | 175 | 1 | 1 | 1 | 2 | 3 | 3 | 3 | 3 | 3 | 3 | 3 | 5 | | | | | | | 2.6 |
| 94AGH | 182 | 1 | 1 | 1 | 1 | 1 | 3 | 3 | 3 | 3 | 4 | 4 | 4 | 4 | 5 | | | | | 2.6 |
| 94AGH | 176 | 1 | 1 | 1 | 1 | 1 | 1 | 3 | 3 | 5 | 5 | 5 | 5 | 5 | | | | | | 2.7 |
| 94AGH | 142 | 1 | 1 | 1 | 2 | 3 | 3 | 3 | 3 | 3 | 3 | 5 | 5 | | | | | | | 2.8 |
| 94AGH | 145 | 1 | 1 | 1 | 3 | 3 | 3 | 3 | 3 | 3 | 4 | 4 | 4 | | | | | | | 2.8 |
| 94AGH | 147 | 1 | 1 | 1 | 1 | 1 | 2 | 3 | 3 | 3 | 3 | 3 | 3 | 3 | 4 | 4 | 4 | 4 | 5 | 2.8 |
| 94AGH | 92 | 2 | 2 | 2 | 3 | 3 | 3 | 3 | 3 | 3 | 3 | 3 | 3 | 3 | 3 | | | | | 2.8 |
| 94AGH | 105 | 2 | 2 | 2 | 2 | 2 | 3 | 3 | 3 | 3 | 3 | 3 | 3 | 3 | 4 | 4 | | | | 2.8 |
| 94AGH | 165 | 2 | 2 | 2 | 3 | 3 | 3 | 3 | 3 | 3 | 4 | | | | | | | | | 2.8 |
| 94AGH | 91 | 1 | 1 | 2 | 2 | 2 | 2 | 2 | 2 | 3 | 3 | 3 | 3 | 3 | 3 | 4 | 4 | 5 | 5 | 5 | 2.9 |
| 94AGH | 122 | 1 | 2 | 2 | 2 | 3 | 3 | 3 | 3 | 5 | 5 | 5 | | | | | | | | 2.9 |
| 94AGH | 117 | 2 | 2 | 2 | 2 | 2 | 2 | 3 | 3 | 3 | 3 | 3 | 3 | 3 | 3 | 5 | 5 | 5 | | 2.9 |
| 94AGH | 102 | 3 | 3 | 3 | 3 | 3 | 3 | 3 | 3 | 3 | 3 | 3 | 3 | | | | | | | 3 |
| 94AGH | 107 | 1 | 2 | 3 | 3 | 3 | 3 | 3 | 3 | 3 | 3 | 3 | 4 | 4 | 4 | | | | | 3 |
| 94AGH | 101 | 1 | 1 | 2 | 2 | 2 | 2 | 2 | 3 | 4 | 5 | 5 | 5 | 5 | 5 | | | | | 3.1 |
| 94AGH | 123 | 1 | 1 | 1 | 2 | 2 | 2 | 3 | 3 | 5 | 5 | 5 | 5 | 5 | | | | | | 3.1 |
| 94AGH | 153 | 2 | 2 | 2 | 3 | 3 | 3 | 3 | 3 | 3 | 4 | 4 | 4 | 5 | | | | | | 3.1 |
| 94AGH | 118 | 2 | 2 | 2 | 2 | 2 | 3 | 3 | 3 | 3 | 3 | 5 | 5 | 5 | 5 | | | | | 3.2 |
| 94AGH | 140 | 2 | 3 | 3 | 3 | 3 | 3 | 4 | 4 | 4 | 4 | | | | | | | | | 3.3 |
| 94AGH | 96 | 3 | 3 | 3 | 3 | 3 | 4 | 4 | | | | | | | | | | | | 3.3 |
| 94AGH | 94 | 3 | 3 | 3 | 3 | 3 | 3 | 3 | 4 | 4 | 4 | | | | | | | | | 3.3 |
| 94AGH | 150 | 3 | 3 | 3 | 3 | 3 | 3 | 3 | 3 | 3 | 3 | 4 | 4 | 4 | 5 | | | | | 3.4 |
| 94AGH | 90 | 3 | 3 | 3 | 3 | 3 | 3 | 3 | 3 | 3 | 4 | 4 | 4 | 4 | 4 | 4 | | | | 3.4 |
| 94AGH | 134 | 1 | 1 | 1 | 2 | 3 | 3 | 3 | 4 | 4 | 4 | 4 | 5 | 5 | 5 | 5 | 5 | | | 3.5 |
| 94AGH | 180 | 1 | 3 | 3 | 3 | 3 | 3 | 3 | 3 | 3 | 3 | 5 | 5 | 5 | 5 | 5 | | | | 3.5 |
| 94AGH | 149 | 2 | 3 | 3 | 3 | 3 | 3 | 3 | 3 | 3 | 4 | 4 | 4 | 4 | 5 | 5 | 5 | 5 | | 3.6 |
| 94AGH | 146 | 3 | 3 | 3 | 3 | 3 | 4 | 4 | 4 | 4 | 4 | 4 | 5 | | | | | | | 3.8 |
| 94AGH | 141 | 3 | 3 | 4 | 4 | 4 | 4 | 4 | 4 | 4 | 4 | 4 | 4 | 4 | 4 | | | | | 3.9 |
| 94AGH | 113 | 3 | 3 | 3 | 3 | 3 | 4 | 4 | 5 | 5 | 5 | 5 | | | | | | | | 3.9 |
| 94AGH | 188 | 3 | 3 | 4 | 4 | 4 | 4 | 4 | 4 | 4 | 4 | 4 | 5 | | | | | | | 3.9 |
| 94AGH | 93 | 3 | 3 | 3 | 3 | 3 | 4 | 4 | 4 | 4 | 5 | 5 | 5 | 5 | | | | | | 3.9 |
| 94AGH | 130 | 4 | 4 | 4 | 4 | 4 | 4 | 4 | 4 | 4 | 4 | 4 | 4 | 4 | 4 | 4 | | | | 4 |
| 94AGH | 152 | 3 | 4 | 4 | 4 | 4 | 4 | 4 | 4 | 4 | 4 | 4 | 4 | 4 | 4 | 5 | 5 | | | 4.1 |
| 94AGH | 128 | 3 | 3 | 3 | 3 | 4 | 4 | 4 | 4 | 5 | 5 | 5 | 5 | 5 | | | | | | 4.1 |
| 94AGH | 129 | 3 | 3 | 3 | 3 | 3 | 4 | 4 | 4 | 4 | 4 | 5 | 5 | 5 | 5 | 5 | 5 | 5 | 5 | 4.2 |
| 94AGH | 163 | 4 | 4 | 4 | 4 | 4 | 4 | 4 | 4 | 4 | 4 | 4 | 5 | 5 | 5 | 5 | | | | 4.2 |
| 94AGH | 177 | 4 | 4 | 4 | 4 | 4 | 4 | 4 | 4 | 4 | 5 | 5 | 5 | | | | | | | 4.2 |
| 94AGH | 116 | 4 | 4 | 4 | 4 | 4 | 4 | 4 | 4 | 4 | 4 | 5 | 5 | 5 | 5 | 5 | | | | 4.3 |
| 94AGH | 110 | 3 | 4 | 4 | 4 | 5 | 5 | 5 | 5 | | | | | | | | | | | 4.4 |
| 94AGH | 95 | 4 | 4 | 4 | 5 | 5 | | | | | | | | | | | | | | 4.4 |
| 94AGH | 155 | 4 | 4 | 4 | 5 | 5 | 5 | 5 | 5 | 5 | 5 | 5 | 5 | 5 | 5 | 5 | 5 | | | 4.8 |
| 94AGH | 178 | 4 | 4 | 5 | 5 | 5 | 5 | 5 | 5 | 5 | 5 | 5 | 5 | 5 | 5 | | | | | 4.9 |
| 94AGH | 131 | 5 | 5 | 5 | 5 | 5 | 5 | 5 | 5 | 5 | 5 | 5 | 5 | 5 | | | | | | 5 |
| Hope | 84 | 1 | 1 | 1 | 1 | 1 | 1 | 1 | 1 | 1 | 1 | 1 | 1 | 2 | 2 | 2 | 2 | | | 1.2 |
| Celebrity | | 5 | 5 | 5 | 5 | 5 | 5 | 5 | 5 | 5 | 5 | 5 | 5 | 5 | 5 | | | | | 5.0 |

The above results confirm the results from the F2 plants described in Example 3. The homozygous resistant (94FH98, 94FH99, 94FH114, 94FH120, 94FH121, 94FH148, 94FH162, 94FH170) and susceptible (94FH95, 94FH110, 94FH116, 94FH128, 94FH129, 94FH155, 94FH178, 94FH188) plants identified in the F2 plants gave the same disease rating in the F3 plants. If resistance was conferred by a number of genes (multigenic complex), then it would not segregate in the 3:1 ratio and the homozygous resistant plants would not be identified as easily and as rapidly as demonstrated.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

We claim:

1. A method for producing tomato plants which are resistant to the tomato strain of *Phytophthora infestans* races 0 and 1, the method comprising the steps of:

a. providing a *Lycopersicon pimpinellifolium* plant designated as LA 2533 having ATCC Accession Number 97382;

b. crossing the *Lycopersicon pimpinellifolium* plant provided in step a with a *Lycopersicon esculentum* plant;

c. collecting the seeds resulting from the cross in step b;

d. regenerating the seeds into plants;

e. inoculating the plants with the tomato strain of *Phytophthora infestans* races 0 and 1;

f. evaluating the plants of step e for resistance to *Phytophthora infestans* races 0 and 1;

g. identifying plants which are resistant to *Phytophthora infestans* races 0 and 1; and h. selecting the plants that are resistant to *Phytophthora infestans* races 0 and 1.

2. The method of claim 1 wherein the plants are evaluated using a disease rating scale, wherein said disease rating scale comprises a numerical system from 1 to 5 where 1 corresponds to no or small lesions on the foliage only; 2 corresponds to no or small lesions on the foliage, plus expanding foliage lesions and small lesions (2 mm diameter) on the petiole; 3 corresponds to no or small lesions on the foliage, expanding foliage lesions and small lesions (2 mm diameter) on the petiole, plus expanding lesions on the petiole; 4 corresponds to no or small lesions on the foliage, expanding foliage lesions and small lesions (2 mm diameter) on the petiole, expanding lesions on the petiole, plus small lesions (2 mm diameter) on the stem; and 5 corresponds to no or small lesions on the foliage, expanding foliage lesions and small lesions (2 mm diameter) on the petiole, expanding lesions on the petiole, small lesions (2 mm diameter) on the stem, plus expanding lesions on the stem or a dead plant.

3. The method of claim 1 wherein the plants are evaluated using a disease rating scale, wherein said disease rating scale comprises a numerical system from 1 to 5 and 1 corresponds to no or small lesions on the foliage only; 2 corresponds to no or small lesions on the foliage, plus expanding foliage lesions and small lesions (2 mm diameter) on the petiole; 3 corresponds to no or small lesions on the foliage, expanding foliage lesions and small lesions (2 mm diameter) on the petiole, plus expanding lesions on the petiole; 4 corresponds to no or small lesions on the foliage, expanding foliage lesions and small lesions (2 mm diameter) on the petiole, expanding lesions on the petiole, plus small lesions (2 mm diameter) on the stem; and 5 corresponds to no or small lesions on the foliage, expanding foliage lesions and small lesions (2 mm diameter) on the petiole, expanding lesions on the petiole, small lesions (2 mm diameter) on the stem, plus expanding lesions on the stem or a dead plant.

4. The method of claim 1 further comprising the steps of backcrossing the plants in step h with *Lycopersicon esculentum* plants having desirable phenotypic traits for a sufficient number of generations to obtain *Lycopersicon esculentum* plants that are resistant to *Phytophthora infestans* races 0 and 1 and have desirable phenotypic traits.

5. The method of claim 1 further comprising the steps of self-crossing the plants of step h for a sufficient number of generations to obtain plants that are fixed for an allele that confers resistance to the tomato strain of *Phytophthora infestans* races 0 and 1 in the plants; and backcrossing the plants with *Lycopersicon esculentum* plants having desirable phenotypic traits to obtain *Lycopersicon esculentum* plants that are resistant to *Phytophthora infestans* races 0 and 1 and have desirable phenotypic traits.

6. The method of claim 1 wherein the plants are evaluated using a disease rating scale, wherein said disease rating scale comprises a numerical system from 1 to 5 where 1 corresponds to no or small lesions on the foliage only; 2 corresponds to no or small lesions on the foliage, plus expanding foliage lesions and small lesions (2 mm diameter) on the petiole; 3 corresponds to no or small lesions on the foliage, expanding foliage lesions and small lesions (2 mm diameter) on the petiole, plus expanding lesions on the petiole; 4 corresponds to no or small lesions on the foliage, expanding foliage lesions and small lesions (2 mm diameter) on the petiole, expanding lesions on the petiole, plus small lesions (2 mm diameter) on the stem; and 5 corresponds to no or small lesions on the foliage, expanding foliage lesions and small lesions (2 mm diameter) on the petiole, expanding lesions on the petiole, small lesions (2 mm diameter) on the stem, plus expanding lesions on the stem or a dead plant.

7. A tomato plant which is resistant to the tomato strain of *Phytophthora infestans* races 0 and 1 produced by the method of claim 1.

8. Seed produced by the plant of claim 7.

9. A tomato plant which contains an allele that confers resistance to the tomato strain of *Phytophthora infestans* races 0 and 1 produced by the method of claim 1.

10. Seed produced by the plant of claim 9.

11. A method of producing seeds that result in tomato plants resistant to the tomato strain of *Phytophthora infestans* races 0 and 1, the method comprising the steps of:

a. providing a *Lycopersicon pimpinellifolium* in plant designated as LA 2533 having ATCC Accession Number 97382;

b. crossing the *Lycopersicon pimpinellifolium* plant provided in step a with a *Lycopersicon esculentum* plant; and c. collecting seeds resulting from the cross in step b, which when planted, produce tomato plants which are resistant to the tomato strain of *Phytophthora infestans* races 0 and 1.

12. A method for producing seeds that result in tomato plants resistant to the tomato strain of *Phytophthora infestans* races 0 and 1, the method comprising the steps of:

a. providing a *Lycopersicon pimpinellifolium* plant designated as LA 2533 having ATCC Accession Number 97382;

b. crossing the *Lycopersicon pimpinellifolium* plant provided in step a with a *Lycopersicon esculentum* plant;

c. collecting the seeds resulting from the cross in step b;

d. regenerating said seeds into plants;

e. inoculating the plants with the tomato strain of *Phytophthora infestans* races 0 and 1;

f. evaluating the plants of step e for resistance to *Phytophthora infestans* races 0 and 1;

g. identifying plants which are resistant to *Phytophthora infestans* races 0 and 1;

h. selecting the plants that are resistant to *Phytophthora infestans* races 0 and 1;

i. backcrossing the plants in step h with *Lycopersicon esculentum* plants having desirable phenotypic traits for a sufficient number of generations to obtain *Lycopersicon esculentum* plants that are resistant to *Phytophthora infestans* races 0 and 1 and have desirable phenotypic traits; and j. collecting the seeds produced from the plants of step i which when planted, produce tomato plants which are resistant to the tomato strain of *Phytophthora infestans* races 0 and 1.

13. A method for producing seeds that result in tomato plants resistant to the tomato strain of *Phytophthora infestans* races 0 and 1, the method comprising the steps of:

a. providing a *Lycopersicon pimpinellifolium* plant designated as LA 2533 having ATCC Accession Number 97382;

b. crossing the *Lycopersicon pimpinellifolium* plant provided in step a with a *Lycopersicon esculentum* plant;

c. collecting the seeds resulting from the cross in step b;

d. regenerating the seeds into plants;

e. inoculating the plants with the tomato strain of *Phytophthora infestans* races 0 and 1;

f. evaluating the plants of step e for resistance to *Phytophthora infestans* races 0 and 1;

g. selecting the plants that are resistant to *Phytophthora infestans* races 0 and 1;

h. self-crossing the plants in step g for a sufficient number of generations to obtain plants that are fixed for an allele that confers resistance to the tomato strain of *Phytophthora infestans* races 0 and 1 in the plants; and i. backcrossing the plants produced in step h with *Lycopersicon esculentum* plants having desirable phenotypic traits to obtain *Lycopersicon esculentum* plants that are resistant to *Phytophthora infestans* races 0 and 1 and have desirable phenotypic traits.

* * * * *